US007524906B2

(12) United States Patent
IJpeij et al.

(10) Patent No.: US 7,524,906 B2
(45) Date of Patent: Apr. 28, 2009

(54) PROCESS FOR THE PREPARATION OF A METAL-ORGANIC COMPOUND COMPRISING AT LEAST ONE IMINE LIGAND

(75) Inventors: Edwin IJpeij, Sittard (NL); Henricus Arts, Munstergeleen (NL); Gerardus van Doremaele, Sittard (NL); Felix Beijer, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/566,979

(22) PCT Filed: Aug. 3, 2004

(86) PCT No.: PCT/EP2004/008714

§ 371 (c)(1),
(2), (4) Date: Jul. 3, 2006

(87) PCT Pub. No.: WO2005/014665

PCT Pub. Date: Feb. 17, 2005

(65) Prior Publication Data

US 2006/0247438 A1    Nov. 2, 2006

(30) Foreign Application Priority Data

Aug. 4, 2003   (EP)   ................... 03077434

(51) Int. Cl.
*C08F 4/642* (2006.01)
*C08F 4/6592* (2006.01)

(52) U.S. Cl. ........................ 526/161; 526/160; 526/165; 556/13; 556/21; 556/53; 502/103; 502/104; 502/155

(58) Field of Classification Search ................ 502/155, 502/103, 104; 556/13, 21, 53; 526/160, 526/161, 165
See application file for complete search history.

(56) References Cited

U.S. PATENT DOCUMENTS 6,114,481 A    9/2000   McMeeking et al.

6,355,744 B1 *  3/2002  von Haken Spence et al. ................ 526/127
2004/0010142 A1 *  1/2004  Nielsen et al. ................ 544/12

FOREIGN PATENT DOCUMENTS

| CA | 2210131 | 1/1999 |
|---|---|---|
| CA | 2243726 | 1/2000 |
| CA | 2243775 | 1/2000 |
| CA | 2243783 | 1/2000 |
| CA | 2261518 | 8/2000 |
| WO | WO 02/070569 | 9/2002 |

OTHER PUBLICATIONS

Mark J. Sarsfield et al; "The reactivity of trimethylsilyliminophosphines towards titanium and zirconium halides"; Journal of the Chemical Society, Dalton Transactions, No. 6; Mar. 21, 2001; pp. 822-827.

* cited by examiner

*Primary Examiner*—Caixia Lu
(74) *Attorney, Agent, or Firm*—Nixon & Vanderhye P.C.

(57) ABSTRACT

The invention relates to a process for the preparation of a metal-organic compound, comprising at least one imine ligand, characterized in that an imine ligand according to formula 1, or the HA adduct thereof, wherein HA represents an acid, of which H represents its proton and A its conjugate base, is contacted with a metal-organic reagent of formula 2 in the presence of at least 1, respectively 2 equivalents of an inorganic or metal-organic base, wherein Y=N-R (formula 1), Y is selected from a substituted carbon, nitrogen or phosphorous atom, R represents a proton, a protic or an aprotic substituent, and the metal organic compound is: $M^V(L_1)k(L_2)l(L_3)_m(L_4)_nX$ (formula 2) wherein: M represents a group 4 or group 5 metal ion, V represents the valency of the metal ion, being 3, 4 or 5, $L_1$, $L_2$, $L_3$, and $L_4$ represent ligands on M and may be equal or different, X represents a group 17 halogen atom, and k, l, m, n=0, 1, 2, 3, 4 with $k+l+m+n+1=V$. The invention further relates to a process for the preparation of a polyolefin by making a metal-organic compound according to the process of the invention, wherein the base is an olefin polymerisation compatible base, which metal-organic compound is activated anywhere in, or before a polymerisation reactor.

10 Claims, No Drawings

PROCESS FOR THE PREPARATION OF A METAL-ORGANIC COMPOUND COMPRISING AT LEAST ONE IMINE LIGAND

This application is the U.S. national phase of international application PCT/EP2004/008714 filed 3 Aug. 2004 which designated the U.S. and claims benefit of EP 03077434.3, dated 4 Aug. 2003, the entire content of which is hereby incorporated by reference.

The invention relates to a process for the preparation of an metal-organic compound comprising at least one imine ligand according to formula 1. Metal-organic compounds thus produced are typically used as precatalyst in the production of polyolefins. Imine ligands for these precatalyst can be guanidine, iminoimidazoline, ketimine or phosphinimine, the manufacturing of which is described in WO 02070569, U.S. Pat. No. 6,114,481 and U.S. Pat. No. 6,063,879 respectively.

The known production processes for phosphinimine comprising metal-organic compounds require at least two steps: (i) the synthesis of a N-trialkylsilyl substituted imine ligand, followed by (ii) contacting this ligand with an metal-organic precursor. However, in the one step process for the manufacturing of the imine ligand, as described in Z. Naturforschung. 29b, 328(1974) (the Staudinger reaction), azide chemistry is required. In this process, the most frequently used azide is azidotrimethylsilane, which is highly toxic and readily hydrolysable, releasing the highly toxic and both temperature and shock sensitive hydrazoic acid. Therefore, mixtures containing (partially) hydrolysed trimethylsilylazide may explosively decompose.

A process for an azide-free preparation of imine ligands (i.c. phosphinimine) is described in Canadian patent application CA 2,261,518. However, this procedure encompasses two reaction steps starting from aminophosphoniumhalides. Another disadvantage of the method described in CA 2,261, 518, is the use of harmful and costly reagents, such as n-butyllithium. Finally, in this procedure the imine ligand is substituted with trimethylsilylchloride, which is removed as such in a subsequent reaction of the imine ligand with the metal-organic precursor. Known production processes for guanidine-, ketimine- and iminoimidazoline comprising metal-organic compounds are described in WO 2070569 and U.S. Pat. No. 6,114,481. They are carried out at low temperature and require in some cases a solvent change.

Disadvantage of the known less dangerous method is thus that at least two steps are required, when starting the process with an aminophosphoniumhalide. Purpose of the present invention is to provide a widely applicable method for the manufacturing of a metal-organic compound from an imine and a metal-organic precursor in one step.

This object is achieved in that at least one imine ligand according to formula 1 where the imine ligand is contacted with a metal-organic reagent of formula 2 in the presence of at least 1 equivalent of an inorganic or metal-organic base, or an HA adduct of an imine ligand according to formula 1, is contacted with a metal-organic reagent of formula 2 in the presence of at least 2 equivalents of an inorganic or metal-organic base, where

 as formula 1, where Y is selected from a substituted carbon, nitrogen, or phosphorous atom and R represents a proton, a protic or an aprotic substitutent, and:

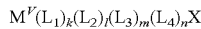 as formula 2, where M represents a group 4 or group 5 metal ion, V represents the valency of the metal ion, being 3, 4 or 5, $L_1$, $L_2$, $L_3$, and $L_4$ represent ligands on M which may be the same or different, X represents a group 17-halogen atom, k, l, m, n =0, 1, 2, 3, 4 with k+l+m+n+l=V, and where HA represents an acid, of which H represents its proton and A its conjugated base.

In this application a base is understood to be an inorganic or metal-organic base. CA 02243775 describes a similar preparation of an metal-organic compound in the presence of an inorganic base. Surprisingly it was found that this reaction could also be carried out in the presence of the cheaper inorganic base like potassium carbonate. Another advantage is the formation of a precipitate which can be filtered off easier than the precipitate which is formed with the organic base used in CA 02243775. Still another advantage is the fact that inorganic bases are environmentally friendly and allows a broader range of solvents used in the process of the invention. An advantage of the metal-organic base is that with this base the hydrocarbylated metal-organic compound can be prepared in a one step process. In the known process the metal-organic dichloride has to be hydrocarbylated in a second reaction step in case this is required for exampled to use the metal-organic compound in a polymerisation process using a boron comprising activator. Another advantage of the process of the invention is the use of the HA adduct of the imine, which can be prepared easier than the imine of the state of the art.

With the method of the invention a metal-organic compound, suitable as precatalyst in olefin polymerisation, is prepared in one step. An additional advantage of the method of the invention is, that during the process hardly any by-products are formed, so that further purification is not necessary (or very limited with respect to state of the art processes). The metal-organic compound prepared by the method of the invention has a higher purity than a metal-organic compound prepared via known production processes and can be used as such in olefin polymerisation processes. An additional advantage of the process of the invention is that the process can be carried out at room temperature, whereas the reaction of the N-trialkylsilyl substituted imine ligand with the metal-organic reagent has to be often carried out at elevated temperatures.

The imine derivative or its HA adduct, as represented in formula 1, is substituted by an Y- and an R group. In the method of the invention, the Y group consists of a substituted carbon, nitrogen or phosphorous atom. If Y represents a substituted carbon atom, the number of substituents is 2. If Y represents a substituted nitrogen atom, the number of substituents is 1 and the number of substituents is 1 or 3 if Y represents a phosphorous atom, depending on the valency of the phosphorous atom.

Substituents on carbon, nitrogen or phosphorous may be equal or different, optionally linked with each other, optionally having heteroatoms. Substituents may be protic or aprotic. A protic substituent is defined here as a substituent, which has at least one, group 15 or group 16 atom containing at least one proton.

Examples of protic subsituents include $C_1$-$C_{20}$ linear, branched or cyclic hydrocarbyl radicals, substituted with a group 15 or 16 atom bearing at least one hydrogen atom. Preferred protic substituents include phenolic radicals, pyrrolic radicals, indolic radicals, and imidazolic radicals.

The substituent is called aprotic if the substituent lacks a group containing a group 15 or group 16 atom bearing a proton. An unsubstituted aprotic hydrocarbyl radical can be a $C_1$-$C_{20}$ linear, branched or cyclic radical, a hydrogen atom, a halogen atom, a $C_{1-8}$alkoxy radical, a $C_{6-10}$aryl or aryloxy radical, an amido radical, or a $C_{1-20}$ hydrocarbyl radical unsubstituted or substituted by a halogen atom, a $C_{1-8}$ alkoxy radical, a $C_{6-10}$ aryl or aryloxy radical, an amido radical, a silyl radical of the formula 4, or a germanyl radical of the formula 5.

The substituent R can be H, or being equal as these for the substituent on Y.

Examples of imine ligands according to formula (1) thus include: guanidines, iminoimidazolines, phosphinimines, phenolimines, pyrroleimines, indoleimines and imidazoleimines.

R may be linked with Y, thus forming a ring system, optionally comprising heteroatoms, or optionally comprising functional groups. Examples of ligands comprising such ring systems include: 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole.

In a preferred embodiment of the method of the invention, R represents a hydrogen atom and Y is selected from the group consisting of:

i) a phosphorus substituent according to the formula:

(formula 3)

wherein each $R^{1j}$, with j=1-3 is independently selected from the group consisting of a hydrogen atom, a halogen atom, a $C_{1-8}$alkoxy radical, a $C_{6-10}$aryl or aryloxy radical, an amido radical, or a $C_{1-20}$ hydrocarbyl radical unsubstituted or substituted by a halogen atom, a $C_{1-8}$ alkoxy radical, a $C_{6-10}$ aryl or aryloxy radical, an amido radical, a silyl radical of the formula:

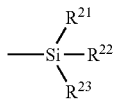

(formula 4)

or a germanyl radical of the formula:

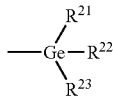

(formula 5)

wherein $R^{2j}$, with j=1-3, is independently selected from the group consisting of hydrogen, a $C_{1-8}$ alkyl or alkoxy radical, $C_{6-10}$ aryl or aryloxy radicals, each substituent $R^{1j}$ or $R^{2j}$ may be linked with another $R^{1j}$ or $R^{2j}$ respectively to form a ring system, ii) a substituent according to formula 6:

(formula 6)

wherein each of $Sub^1$ and $Sub^2$ is independently selected from the group consisting of hydrocarbyl radicals having from 1 to 30 carbon atoms; silyl radicals, (substituted) amido radicals and (substituted) phosphido radicals, and wherein $Sub^1$ and $Sub^2$ may be linked with each other to form a ring system.

Preferably $Sub^1$ and $Sub^2$ are each independently selected from the group of C1-C20 hydrocarbyl radicals, or substituted amido radicals optionally linked by a bridging moiety.

Preferably the metal-organic compound is contacted with the HA adduct of an imine ligand, with more preference a phosphinimine ligand in the presence of at least two equivalents of a base. A process for a less dangerous azide-free preparation of phosphinimine ligands is described in Canadian patent application CA 2,261,518. In a first step a trialkyl aminophosphoniumhalide (which is the HX adduct of trialkylphosphinimine) is reacted with a base to a trialkyl phosphinimide salt, where after this trialkyl phosphinimide salt is quenched with trimethyl silylchloride (TMSCl). The thus formed trialkyl silyl substituted phosphinimine ligand is subsequently reacted in a third step with $CpTiCl_3$ to the metal organic compound. A disadvantage of the 3 step method described in CA 2,261,518, is the use of harmful and costly reagents, such as n-butyllithium. Another purpose of the present invention is therefore to provide a widely applicable method for the manufacturing of a metal-organic compound from an aminophosphoniumhalide and a metal-organic reagent in one step. This aim is achieved in a process wherein an HA adduct of a phosphinimine ligand (e.g. aminophosphonium halide) according to formula 1 is contacted with a metal-organic reagent of formula 2 in the presence of at least 2 equivalents of a base, wherein HA represents an acid, of which H represents its proton and A its conjugate base, with Y=NH being the ligand in formula 1, wherein Y is represented by formula 3.

In the process of the invention, HA represents an acid, of which H represents its proton and A its conjugate base. Examples of A are halogenides, such as fluoride, chloride, bromide, or iodide, sulfate, hydrogensulfate, phosphate, hydrogenphosphate, dihydrogenphosphate, carbonate, hydrogencarbonate, aromatic or aliphatic carboxylates, cyanide, tetrafluoroborate, (substituted) tetraphenylborates, fluorinated tetraarylborates, alkyl or aryl sulfonates.

The "number of equivalents of a base" is understood to be the amount of equivalents with respect to the number of imine ligands, or functionalities in the event that one ligand comprises more than one imine functionality. With "at least 1, respectively 2 equivalents of a base", and later on in the application "at least 3, respectively 4 equivalents of a base", is meant that at least 1, respectively 3 equivalents of a base are required when the imine ligand as such is used, but that at least 2, respectively 4 equivalents are required, in case the HA adduct of the imine ligand is used.

The metal-organic reagent used in the method of the invention is a reagent according to formula 2. In this formula $L_1$ to $L_4$ can independently be a monoanionic ligand or a group 17 halogen atom.

Examples of monoanionic ligands are: halides like a fluoride, chloride, bromide or iodide, (un)substituted aliphatic or aromatic hydrocarbyls, like $C_1$-$C_{20}$ hydrocarbyl radicals, aryloxy or alkyloxy, cyclopentadienyls, indenyls, tetrahydroindenyls, fluorenyls, tetrahydrofluorenyls, and octahydrofluorenyls, amides, phosphides, sulfides, ketimides, guanidines, iminoimidazolines, phosphinimides, substituted imines, like (hetero)aryloxyimines, pyrroleimines, indoleimines, imidazoleimines or (hetero)aryloxides.

Preferred monoanionic ligands include: fluoride, chloride, bromide, iodide, $C_1$-$C_{20}$ hydrocarbyl radicals, cyclopentadienyl, $C_1$-$C_{20}$ hydrocarbyl substituted cyclopentadienyls, halogen substituted $C_1$-$C_{20}$ hydrocarbyl substituted cyclopentadienyls, indenyl, $C_1$-$C_{20}$ hydrocarbyl substituted indenyls, halogen substituted $C_1$-$C_{20}$ hydrocarbyl substituted indenyls, fluorenyls, $C_1$-$C_{20}$ hydrocarbyl substituted fluorenyls, halogen substituted $C_1$-$C_{20}$ hydrocarbyl substituted fluorenyls, $C_1$-$C_{45}$ substituted phosphinimides, $C_1$-$C_{20}$ substituted ketimides, $C_1$-$C_{30}$ substituted guanidines, $C_1$-$C_{30}$ iminoimidazolines.

Most preferably monoanionic ligands are selected from fluoride, chloride, bromide, iodide, cyclopentadienyl, $C_1$-$C_{20}$ hydrocarbyl (optionally containing hetero- or group 17 halogen atoms), substituted cyclopentadienyls, indenyl, $C_1$-$C_{20}$ hydrocarbyl substituted indenyls, and halogen substituted $C_1$-$C_{20}$ hydrocarbyl substituted indenyls.

Depending on the valency of the metal of the metal-organic reagent, preferably at least one $L_1$, $L_2$, $L_3$, or $L_4$ represents a group 17 atom. If the valency of the metal V=3, one or two ligands L may represent a group 17 atom. If V=4, two or three ligands L may represent a group 17 atom. If V=5, two to four ligands L may represent a group 17 atom. Preferred group 17 atom ligands are fluoride, chloride, bromide or iodide atoms. The most preferred group 17 atom ligand is chloride. In a most preferred embodiment, at least one of the ligands L is chosen from cyclopentadienyl, $C_1$-$C_{20}$ hydrocarbyl (optionally containing hetero- or group 17 halogen atoms), substituted cyclopentadienyls, indenyl, $C_1$-$C_{20}$ hydrocarbyl substituted indenyls, and halogen substituted $C_1$-$C_{20}$ hydrocarbyl substituted indenyls. $C_1$-$C_{20}$ hydrocarbyl (optionally containing hetero- or group 17 halogen atoms) also includes aryloxy or alkyloxy, octahydrofluorenyls, amides, phosphides, sulfides, ketimides, guanidines, iminoimidazolines, phosphinimides, substituted imines, like (hetero)aryloxyimines, pyrroleimines, indoleimines, imidazoleimines and (hetero) aryloxides.

In the method of the invention an imine ligand or the HA adduct thereof according to formula 1, is contacted with a metal-organic reagent of formula 2 in the presence of at least 1, respectively 2, equivalents of a base. In this application a base is understood to be an inorganic base or a metal-organic base. An inorganic base is a metal or a metal salt capable of accepting at least one proton. A metal-organic base is a carbanion of an element of group 1, 2, 12 or 13. Examples of a base include, carboxylates (for example potassium acetate), fluorides, hydroxides, cyanides, amides and carbonates of Li, Na, K, Rb, Cs, ammonium and the group 2 metals Mg, Ca, & Ba, the alkali metal (Li, Na, K, Rb, Cs) phosphates and the phosphate esters (eg. $C_6H_5$ OP(O)(ONa)$_2$ and related aryl and alkyl compounds) and their alkoxides and phenoxides, thallium hydroxide, alkylammonium hydroxides and fluorides. Some of these bases may be used in conjunction with a phase transfer reagent, such as for example tetraalkylammonium-, tetraalkylphosphonium salts or crown ethers. Also stronger bases may be applied, like carbanions such as hydrocarbanions of group 1, group 2, group 12 or group 13 elements. Also the metallic alkalimetals of group 1 may be applied as a base.

Preferred bases include, organolithium compounds, or organomagnesium compounds, alkali metals, group 1 hydrides or group 2 hydrides More preferred bases are organolithium compounds, organomagnesium compound, sodium hydride or calciumhydride.

Examples of organomagnesium compounds are: methylmagnesiumhalides, phenylmagnesiumhalides, benzylmagnesiumhalides, biphenylmagnesiumhalides, naphtylmagnesiumhalides, tolylmagnesiumhalides, xylylmagnesiumhalides, mesitylmagnesiumhalides, dimethylresorcinolmagnesiumhalides, N,N-dimethylanilinemagnesiumhalides, dimethylmagnesium, diphenylmagnesium, dibenzylmagnesium, bis(biphenyl)magnesium, dinaphtylmagnesium, ditolylmagnesium, dixylylmagnesium, dimesitylmagnesium, bis(dimethylresorcinol)magnesium, bis(N,N-dimethylaniline)magnesium.

Examples of organolithium compounds are: methyllithium, phenyllithium, benzyllithium, biphenyllithium, naphtyllithium, dimethylresorcinollithium, N,N-dimethylanilinelithium.

In order to make a polyolefin by a borane or borate activatable metal-organic compound, the halide groups of the metal-organic compound from the process of the invention have to be alkylated or arylated in an additional reaction step. This can be done for example with an organolithium compound or an organo magnesium compound. Surprisingly it has been found that such alkylated or arylated metal-organic compound can also be prepared in one step by the process of the invention by carrying out the process in the presence of at least 3, respectively 4 equivalents of an organomagnesium compound or an organolithium compound as a base. This holds for a metal-organic reagent comprising 3 halogen ligands reacting with 1 imine functionality only. One skilled in the art will understand that metal-organic reagents with 4 or 5 halogen ligands will require at least 4 respectively 5 equivalents of a base in stead of at least 3, or 5 respectively 6 equivalents in stead of 4.

The process of the invention is preferably carried out in a solvent. Suitable solvents are solvents that do not react with the metal-organic reagent or the metal-organic compound formed in the process of the invention. Examples of suitable solvents include aromatic and aliphatic hydrocarbons, halogenated hydrocarbons, amides of the aliphatic carboxylic acids and primary, or secondary amines, DMSO, nitromethane, acetone, acetonitrile, benzonitrile, ethers, polyethers, cyclic ethers, lower aromatic and aliphatic ethers, or esters, and mixtures thereof. Preferred solvents include aromatic or aliphatic hydrocarbons or mixtures thereof.

The process of the invention can be carried out, by adding at least 1, respectively at least 2 equivalents of a base to a mixture of the imine ligand or its HA adduct and the metal-organic reagent thus forming a reaction mixture. The desired metal-organic compound is often formed instantaneously. Excess of a base may be applied without negative effects on the reaction product.

During the reaction, a salt is formed. The reaction mixture as obtained by contacting an imine or its HA adduct may be used as precatalyst in a polyolefin polymerisation without an additional filtration step if the salt formed during the reaction is compatible with the polymerisation process. If a salt free metal-organic compound is required, the salt can be removed by using a filtration. Depending on the solubility of the metal-organic compound, the mixture may be heated and then filtered. An advantage of the present invention is that the filtrate may be used as such without further purification in a following process, such as an alkylation or arylation step or the polymerisation process. If desired, the metal-organic compound may be isolated by distillation of the solvent, by precipitation or by crystallisation from a suitable solvent.

The invention further relates to a process for the preparation of a polyolefin as described in claim 13. Such an olefin polymerisation can be carried out in solution, slurry or in the gas phase.

In a preferred embodiment of the olefin polymerisation the (alkylated) metal-organic compound is formed in situ. By in situ preparation is meant in this context, that the metal-organic compound is made and subsequently activated in or anywhere before the reactor of the polymerisation equipment by contacting an imine or its HA adduct with an metal-organic reagent in the presence of an olefin polymerisation compatible base. Examples of bases compatible with the olefin polymerisation process include, organomagnesium compound, organolithium reagents, organozinc reagents, organoaluminum reagents. More preferred bases are: organomagnesium compound, organolithium reagents, organozinc reagents, organoaluminum reagents. Most preferred bases are dibutylmagnesium, n-butyllithium, $C_1$-$C_{20}$ dihydrocarbylzinc derivatives, diisobutylaluminium hydride, $C_1$-$C_{20}$ trihydrocarbyl aluminiums, or aluminoxanes. In the case where aluminoxanes are applied as a base, the base can be the activator.

In the olefin polymerisation according to the invention, R preferably represents a proton and Y is preferably selected from the group consisting of:

i) a phosphorus substituent according to formula 3 of claim 2 or:

ii) a substituent according to formula 6 of claim 2.

Advantages of the process of the invention are: mild conditions, higher yields, higher reaction rates and smaller amounts of by-products. The (alkylated) metal-organic compounds as obtained by the invented process can be used without further purification in the olefin polymerisation resulting in more active catalysts.

The invention will be elucidated with some non-limiting examples:

General Part

Experiments were performed under a dry and oxygen-free nitrogen atmosphere using Schlenk-line techniques. $^1$H-NMR, $^{13}$C-NMR-spectra and $^{31}$P-NMR-spectra were measured on a Bruker Avance 300 spectrometer. Diethyl ether and ligroin were distilled from sodium/potassium alloy; THF and toluene from potassium and sodium, respectively, all having benzophenone as indicator. Tri-ethylamine was distilled from calciumhydride before use. Other starting materials were used as obtained.

EXAMPLE I

One-Step Preparation of (Cp—$C_6F_5$)Ti(NP(t-Bu)$_3$)Me$_2$ from Tri-tert-butyl Aminophosphonium Chloride (tBu$_3$PClNH$_2$) and Cp($C_6F_5$)TiCl$_3$ Using methylmagnesiumbromide as Base To an orange mixture of $C_6F_5$CpTiCl$_3$ (1.00 g, 2.59 mmol) and t-Bu$_3$PClNH$_2$ (0.68 g, 2.59 mmol) in toluene (60 mL) and THF (20 mL) was added a MeMgBr solution in ether (3.0M, 4.0 mL, 12 mmol) at –20° C. The reaction mixture was stirred for 45 minutes and subsequently dried in vacuo. The residue was extracted with boiling ligroin (20 and 40 mL respectively). The solvents were removed in vacuo resulting in 1.33 g (98%) of (Cp—$C_6F_5$)Ti(NP(t-Bu)$_3$)Me$_2$ with no detectable amounts of by-product.

EXAMPLE II

Synthesis of 1,3-bis(2,6-dimethylphenyl)-iminoimidazoline cyclopentadienyl titanium dimethyl Using methylmagnesium Bromide as Base To a suspension of 1,3-bis(2,6-dimethylphenyl)-iminoimidazoline (2.93 g, 10.0 mmol) and cyclopentadienyltitanium trichloride (2.19 g, 10.0 mmol) in toluene (100 mL) was added methylmagnesiumbromide (11 mL of a 3.0 M solution in diethyl ether, 33 mmol) at –80° C. during 10 minutes. The mixture was allowed to warm to ambient temperature to give a yellow suspension. THF (30 mL) was added, and the mixture was stirred for 15 hours. The light yellow suspension was evaporated to dryness. The residue was extracted with boiling ligroin (100 mL). The resulting suspension was filtered hot. The cake was extracted further with hot ligroin (Three times with 60 mL until the filtrate became colourless). The combined yellow filtrates were partially evaporated under reduced pressure to 50 mL. Cooling to approx. 4° C. afforded yellow crystals, which were filtered and washed with cold ligroin to give 2.05 g (47% yield) of NMR pure 1,3-bis(2,6-dimethylphenyl)-iminoimidazoline cyclopentadienyl titanium dimethyl.

EXAMPLE III

Synthesis of tris(N,N-dimethylamido)phosphoraneimido cyclopentadienyl titanium(IV) dichloride To a solution of cyclopentadienyltitanium trichloride (0.51 g, 2.3 mmol) in toluene (40 mL) was added N,N, N',N',N", N"-hexamethylphosphorimidic triamide (0.41 g, 2.3 mmol). Then, dry K$_2$CO$_3$ (0.5 g, 3.6 mmol) was added. $^{31}$P-NMR reaction monitoring showed that the desired product was formed without any detectable amount of by-product. The reaction mixture was filtered in order to remove the salts which were subsequently extracted with an extra portion of toluene (25 mL). The combined solvents of the filtrate were removed in vacuo to give 0.79 g (yield: 94%) of a yellow crystalline product, which was characterized by $^{31}$P-NMR to be pure tris(N,N-dimethylamido)phosphoraneimido cyclopentadienyl titanium(IV) dichloride.

EXAMPLE IV

Synthesis of tris(N,N-dimethylamido)phosphoraneimido cyclopentadienyl titanium(IV) dimethyl To a solution of cyclopentadienyltitanium trichloride (0.51 g, 2.3 mmol) and N,N,N',N',N",N"-hexamethylphosphorimidic triamide (0.44 g, 2.5 mmol) in toluene (40 mL) and THF (10 mL) was added a solution of methylmagnesium bromide in ether (2.3 mL, 3.0 M, 6.9 mmol) at room temperature. The reaction was exothermal under gas evolution and the colour changed to light yellow. $^{31}$P-NMR reaction monitoring showed that the desired product was formed without any detectable amount of by-product. The solvents were removed in vacuo and the product was extracted from the residue with n-hexane twice (50 mL each). The solvents were removed in vacuo to give 0.59 g (yield: 79%) of a yellow powder, which was characterized by $^1$H- and $^{31}$P-NMR to be tris(N,N-dimethylamido)phosphoraneimido cyclopentadienyl titanium (IV) dimethyl.

The invention claimed is:

1. A one step process for the preparation of a metal-organic compound, comprising contacting at least one imine ligand according to formula 1 with a metal-organic reagent of formula 2 in the presence of at least 1 equivalent of an inorganic or metal-organic base, or wherein an HA adduct of the imine ligand is contacted with a metal-organic reagent of formula 2 in the presence of at least 2 equivalents of an inorganic or metal-organic base, wherein formula 1 is:

wherein Y is selected from a substituted carbon, nitrogen, or phosphorous atom and R represents a proton, a protic or an aprotic substituent, and formula 2 is:

$$M^V(L_1)_k(L_2)_l(L_3)_m(L_4)_nX$$

wherein:
M represents a group 4 or group 5 metal ion,
V represents the valency of the metal ion, which is 3, 4 or 5,
$L_1, L_2, L_3$, and $L_4$ represent ligands on M which may be the same or different,
X represents a group 17-halogen atom,
k, l, m, n=0, 1, 2, 3, 4 with k+l+m+n+1=V, and
wherein HA represents an acid, of which H represents its proton and A its conjugated base.

2. A process according to claim 1 wherein R represents a hydrogen atom and Y is selected from the group consisting of:
(i) a phosphorus substituent defined by the formula:

(formula 3)

wherein each $R^{1j}$, with j=1-3, is independently selected from the group consisting of a hydrogen atom, a halogen atom, a $C_{1-8}$ alkoxy radical, a $C_{6-10}$ aryl or aryloxy radical, an amido radical, a $C_{1-20}$ hydrocarbyl radical unsubstituted or substituted by a halogen atom, a $C_{1-8}$ alkoxy radical, a $C_{6-10}$ aryl or aryloxy radical, an amido radical, a silyl radical of the formula:

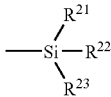

(formula 4)

and a germanyl radical of the formula:

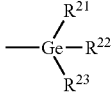

(formula 5)

wherein $R^{2j}$ is independently selected from the group consisting of hydrogen, a $C_{1-8}$ alkyl or alkoxy radical, and $C_{6-10}$ aryl or aryloxy radical, provided each substituent $R^{1j}$ or $R^{2j}$ may be linked with another $R^1$ or $R^2$ to form a ring system, and
(ii) a substituent defined by formula 6:

(formula 6)

wherein each of $Sub^1$ and $Sub^2$ is independently selected from the group consisting of hydrocarbyl radicals having from 1 to 30 carbon atoms; silyl radicals, substituted or unsubstituted amido radicals and substituted or unsubstituted phosphido radicals, and wherein $Sub^1$ and $Sub^2$ may be linked with each other to form a ring system.

3. A process according to claim 1, wherein the base is a carboxylate, or a fluoride, or a hydroxide, or a cyanide, or an amide, or a carbonate of Li, Na, K, Rb, Cs, or a group 2 metal salt selected from Mg, Ca, or Ba, or an alkali metal selected from Li, Na, K, Rb, or Cs of a phosphate or a phosphate ester, or alkoxide of Li, Na, K, Rb or Cs or a phenoxide of Li, Na, K, Rb or Cs, or thallium hydroxide, or a hydrocarbanion of any of the group 1, group 2, group 12 or group 13 elements, or an alkali metal, group 1 hydride or group 2 hydride.

4. A process according to claim 3, wherein the inorganic base is selected from sodium hydride, or calcium hydride.

5. A process according to claim 1, wherein the metal-organic base is selected from an organolithium compound, or an organomagnesium compound.

6. A process according to claim 1, wherein the reaction is carried out in an aprotic solvent.

7. A process according claim 1, wherein the process is carried out in the presence of a phase transfer reagent.

8. A process for the preparation of a polyolefin by preparing a metal-organic compound according to the process of claim 1, wherein the base is an olefin polymerization-compatible base, wherein the metal-organic compound is activated anywhere in, or before a polymerization reactor.

9. A process according to claim 8, wherein the metal-organic compound is used without purification.

10. A process according to claim 8, wherein the metal-organic compound is formed in the polymerization reactor.

* * * * *